United States Patent [19]

Green

[11] Patent Number: 5,124,354
[45] Date of Patent: Jun. 23, 1992

[54] COSMETIC COMPOSITION CONTAINING AN ARYL-SUBSTITUTED ETHYLENE

[75] Inventor: Martin R. Green, Water Stratford, Great Britain

[73] Assignee: Chesebrough Pond's USA Co., Division of Conopco, Inc., Greenwich, Conn.

[21] Appl. No.: 536,135

[22] Filed: Jun. 11, 1990

[30] Foreign Application Priority Data

Jun. 14, 1989 [GB] United Kingdom ............... 8913708

[51] Int. Cl.$^5$ .................... A61K 7/06; A61K 31/015; A01N 1/02
[52] U.S. Cl. .................... 514/520; 424/70; 514/523; 514/525; 514/570; 514/599; 514/616; 514/619; 514/621; 514/622; 514/701; 514/704; 514/705; 514/717; 514/720; 514/733; 514/738; 514/739; 514/741; 514/751; 514/764
[58] Field of Search .......................... 424/70

[56] References Cited

U.S. PATENT DOCUMENTS 4,139,619 8/1977 Chidsey, III .................... 424/45

OTHER PUBLICATIONS

"Blocking of EGF-Dependent Cell Proliferation by EGF Receptor Kinase Inhibitors", Science, vol. 242, Nov. 11, 1988, pp. 933-935.

Primary Examiner—Thurman K. Page
Assistant Examiner—Raj Bawa
Attorney, Agent, or Firm—Milton L. Honig

[57] ABSTRACT

A composition suitable for topical application to mammalian skin or hair for inducing, maintaining or increasing hair growth comprises:
  (i) a special protein tyrosine kinase inhibitor; and
  (ii) a cosmetically acceptable vehicle for the inhibitor.

11 Claims, No Drawings

COSMETIC COMPOSITION CONTAINING AN ARYL-SUBSTITUTED ETHYLENE

FIELD OF THE INVENTION

The invention relates to cosmetic and pharmaceutical compositions for topical application to mammalian skin or hair, containing an aryl-substituted ethylene which is capable of promoting hair growth, especially terminal hair growth on the human scalp.

BACKGROUND

The Hair Growth Cycle

It should be explained that in most mammals, hair does not grow continuously, but undergoes a cycle of activity involving alternate periods of growth and rest. The hair growth cycle can be divided into three main stages, namely:
(i) the growth phase known as anagen, during which the hair follicle penetrates deep into the dermis with the cells of the bulb dividing rapidly and differentiating to form the hair,
(ii) the transitional stage known as catagen, which is heralded by the cessation of mitosis, and during which the follicle regresses upwards through the dermis and hair growth ceases,
(iii) the resting stage known as telogen, in which the regressed follicle contains a small secondary germ with an underlying ball of tightly packed dermal papilla cells.

The initiation of a new anagen phase is revealed by rapid proliferation in the germ, expansion of the dermal papilla and elaboration of basement membrane components. The hair cycle is then repeated many times until, as a consequence of the onset of male pattern baldness, most of the hair follicles spend an increasing proportion of their time in the telogen stage, and the hairs produced become finer, shorter, and less visible; this is known as terminal to vellus transformation.

PRIOR ART

Alleged Baldness Cures

Although there have been many claims in the scientific literature to the promotion or maintenance of hair growth by the topical application of hair tonics and the like, with the possible exception of minoxidil, none has been shown to be sufficiently free from disadvantageous clinical side effects, whether administered topically, orally or systemically, to warrant commercial exploitation as an ethical pharmaceutical, proprietary medicine, or as a cosmetic product. Possibly, the only means which has met with partial success for growing hair on the bald or balding human head is by transplantation of hair to the bald areas. This is, however, an extremely painful operation and is not always successful. Furthermore, it is immediately apparent to the casual observer that the subject has received a hair transplant and it may take many months or even years before hair regrowth, following this operation, assumes an appearance which resembles that of the original naturally growing hair.

Among the many hair regrowth studies that have been reported in the literature, there is included the work of Bazzano as described in PCT International Publication No. WO 85/04577. This publication describes a composition which is useful for increasing the rates of hair growth on mammalian skin, prolonging the anagen phase of the hair growth cycle and for treating various types of alopecias. The composition in question comprises a pyrimidine carbamate.

It has also been reported in U.S. Pat. No. 4,139,619 to Chidsey assigned to the Upjohn Company, that a topical composition comprising minoxidil as the free base or acid addition salt thereof, or certain specified related iminopyrimidines, is useful in stimulating the conversion of vellus hair to growth as terminal hair, as well as increasing the rate of growth of terminal hair.

In spite of the apparent stimulation of hair growth or regrowth reported independently by Bazzano and Chidsey, following topical application of minoxidil or related compounds, there is general concern that systemic side-effects can result, particularly following topical application of minoxidil. Thus it is generally recognised in the medical literature that the side effects of orally administered minoxidil are very serious, and include fluid retention, tachycardia, dyspnea, gynecomastia, fatigue, nausea and cardiotoxicity. There is also evidence that certain side effects have been experienced following topical application of minoxidil.

BACKGROUND TO THE INVENTION

The potential use of tyrosine protein kinase inhibitors as antiproliferative agents is reported by Yaish et al in a paper entitled "Blocking of EGF-Dependent Cell Proliferation by EGF Receptor Kinase Inhibitors" in Science 242 (11) 1988 pages 933-935.

The authors note that a systematic series of low molecular weight protein kinase inhibitors which had progressively increasing ability to inhibit the epidermal growth factor (EGF), stimulated EGF receptor kinase. The most potent compounds were reported effectively to inhibit the EGF-dependent proliferation of A431/-clone 15 cells, with little or no effect on the EGF-independent proliferation of these cells. The authors conclude that these compounds have the potential to become antiproliferative drugs aimed at specific pathological conditions that involve cell proliferation and that can be linked to the expression of specific protein tyrosine kinases.

During studies into the effects of these tyrosine protein kinase inhibitors on the skin of the rat, we observed certain unexpected responses which suggested that these substances may be capable of promoting hair growth. This was tested and evidence obtained to substantiate this hypothesis. These substances are hereinafter referred to generally as "inhibitors".

DEFINITION OF THE INVENTION

Accordingly, the invention provides a composition suitable for topical application to mammalian skin or hair for inducing, maintaining or increasing hair growth, which comprises:
(i) as a protein tyrosine kinase inhibitor an effective amount of from 0.0001 to 99% by weight of an aryl-substituted ethylene having the structure (1)

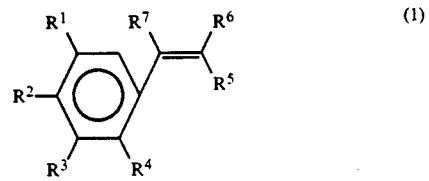

where $R^1$, $R^2$, $R^3$, & $R^4$ are the same or different, and are chosen from

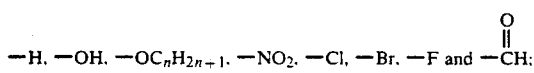

and where $R^5$ & $R^6$ are the same or different, and are chosen from:

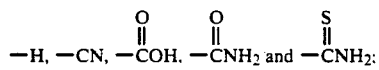

and where $R^7$ is chosen from —H and —OH and where n is an integer of from 1 to 8; and
(ii) from 1 to 99.999% by weight of a cosmetically acceptable vehicle for the inhibitor;
said effective amount of the aryl substituted ethylene present in the composition being sufficient to increase hair growth in the rat, when said composition is applied topically thereto over a period of no more than 3 months, by at least 10% more than that obtainable using a control composition from which the said aryl-substituted ethylene has been omitted, in accordance with the Rat Hair Growth Test.

DISCLOSURE OF THE INVENTION

The aryl-substituted ethylene

According to the invention, the composition comprises an aryl-substituted ethylene having the structure (1)

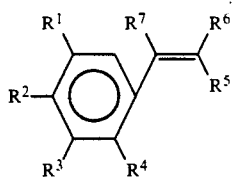

where $R^1$, $R^2$, $R^3$, & $R^4$ are the same or different, and are chosen from

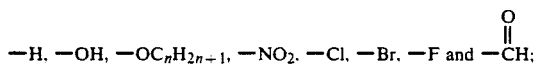

and where $R^5$ & $R^6$ are the same or different, and are chosen from:

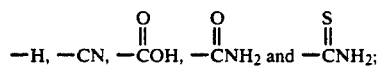

and where $R^7$ is chosen from —H and —OH and where n is an integer of from 1 to 8.

The composition according to the invention can also comprise mixtures of said inhibitors.

Examples of the inhibitors are

| | Inhibitor No in Examples |
|---|---|
| 1-carboxy-2-(4-hydroxyphenyl)ethylene having the structure: | 1. |
| 1,1-dicarboxy-2-(4-hydroxyphenyl)ethylene having the structure: | 2. |
| 1,1-dicyano-2-(4-hydroxyphenyl)ethylene having the structure: | 3. |
| 1-carboxy-2-(3,4-dihydroxyphenyl)ethylene having the structure: | 4. |
| 1,1-dicyano-2-(3-hydroxyphenyl)ethylene having the structure: | 5. |
| 1-cyano-1-carboxy-2-(2,5-dihydroxyphenyl)ethylene having the structure: | 6. |
| 1-carboxy-1-cyano-2-(3,4-dihydroxphenyl)ethylene having the structure: | 7. |
| 1,1-dicyano-2-(3,4-dihydroxyphenyl)ethylene having the structure: | 8. |

| | Inhibitor No in Examples |
|---|---|
| 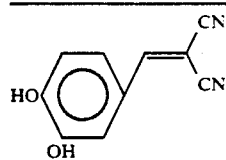 1,1-dicyano-2-(3-methoxy-4,5-dihydroxyphenyl)ethylene having the structure: | 9. |
| 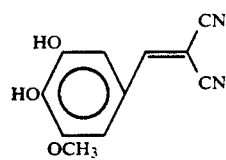 1,1-dicyano-2-(3,4,5-trihydroxyphenyl)ethylene having the structure: | 10. |
| 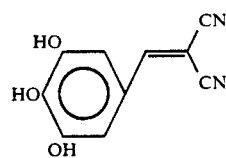 1-amido-1-cyano-2-(3,4-dihydroxyphenyl)ethylene having the structure: | 11. |
| 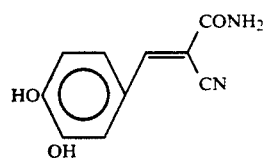 1-thioamido-1-cyano-2-(3,4-dihydroxyphenyl)ethylene having the structure: | 12. |
| 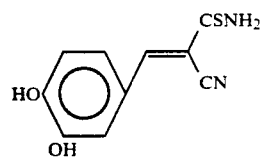 1-cyano-2-(4-hydroxyphenyl)ethylene having the structure: | 13. |
| 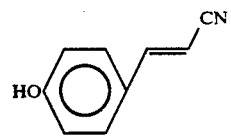 1,1-dicyano-2-(3-hydroxy-4-nitrophenyl)ethylene having the structure: | 14. |
| 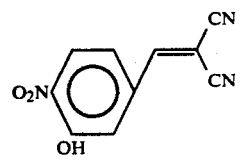 1,1-dicyano-2-hydroxy-2-(4-hydroxyphenyl)ethylene having the structure: | 15. |

| | Inhibitor No in Examples |
|---|---|
| 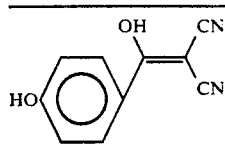 1,1-dicyano-2-(3-methoxy-4-hydroxyphenyl)ethylene having the structure: | 16. |
| 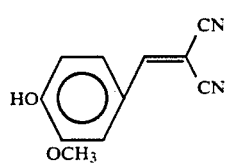 1,1-dicyano-2-(3,5-dihydroxyphenyl)ethylene having the structure: | 17. |
| 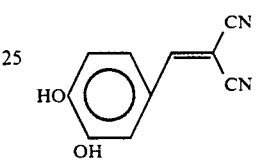 1,1-dicyano-2-hydroxy-2-(3,4,5-trihydroxyphenyl)-ethylene having the structure: | 18. |
| 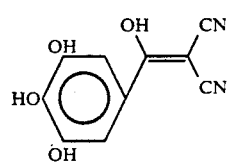 1-carboxy-1-cyano-2-(4-methoxyphenyl)ethylene having the structure: | 19. |
| 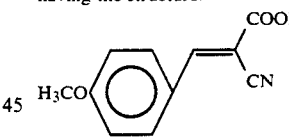 1-carboxy-1-cyano-2-(4-fluorophenyl)ethylene having the structure: | 20. |
| 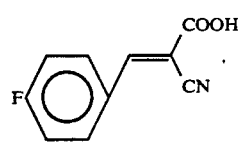 1-carboxy-1-cyano-2-(3-methoxy-4-hydroxyphenyl)-ethylene having the structure: | 21. |
| 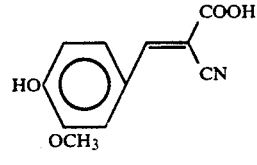 1-carboxy-1-cyano-2-(3,5-dimethoxy-4-hydroxy-phenyl)ethylene having the structure: | 22. |

| -continued | Inhibitor No in Examples |
|---|---|
| 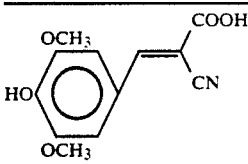 | |
| 1-carboxy-1-cyano-2-(4-hydroxyphenyl)ethylene having the structure: | 23. |
| 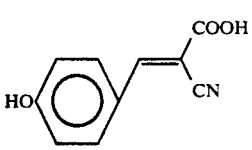 | |
| 1-carboxy-1-cyano-2-(4-phenylcarboxyaldehyde)-ethylene having the structure: | 24. |
|  | |
| 1-cyano-1-carboxy-2-(2,5-dihydroxyphenyl)ethylene having the structure: | 25. |

The total amount of inhibitor present in the composition according to the invention is sufficient to increase hair growth in the rat, the model selected for this test, when said composition is applied topically thereto over a period of no more than 3 months, by at least 10% more than that obtainable using a control composition from which the said ester have been omitted, in accordance with the Rat Hair Growth Test.

Preferably, the amount of the inhibitor should be sufficient to increase hair growth in the rat by at least 20%, more preferably by at least 30%, most preferably by at least 40% and ideally by at least 50%.

The effective amount which is sufficient to induce, maintain or increase hair growth will depend on the effectiveness of the inhibitor, some being more effective than others, but in general, an amount of from 0.0001 to 99%, preferably from 0.01 to 20% by weight of the composition will provide an adequate dose to the skin after topical application.

Preservation of the Composition

The composition according to the invention is preferably preserved in such a manner that it will enjoy an extended shelf life following manufacture and prior to sale and use. Ideally the composition will have an indefinite shelf life.

It is accordingly apparent that the inhibitor is likely to be prone to attack by bacteria, moulds and fungi and other microbial influences, particularly at pH values near that of the skin that characterise the preferred composition. The shelf-life of the composition can therefore be unacceptably short due to the biodegradation of the aryl-substituted ethylene unless steps are taken to preserve the composition.

In order to be preserved, the composition should preferably be free, or substantially free, from viable microbial contaminants that are capable of resulting in microbial spoilage of the composition, and/or biodegradation of the ester prior to topical application of the composition to mammalian skin or hair. It is to be understood, however, that the invention is also concerned with compositions, as herein defined, which may contain viable but dormant microorganisms, such as bacterial spores, provided that the conditions of preservation do not result in substantial proliferation of the microorganisms prior to use of the composition.

Examples of methods that can be employed to achieve preservation of the composition, includes the following:

(i) Sterilisation

The composition according to the invention can be preserved by sterilisation to remove or kill substantially all viable microbial contaminants. This can be achieved for example by irradiation using a lethal dose of gamma rays, by heat sterilisation or by ultrafiltration using techniques that are well established in the pharmaceutical industry.

(ii) Chemical Preservative

The composition according to the invention can also be preserved by including in it a chemical preservative which functions to prevent the growth of or kill bacteria, fungi or other microorganisms.

Examples of chemical preservatives include ethanol, benzoic acid, sodium benzoate, sorbic acid, potassium sorbate, sodium propionate and the methyl, ethyl, propyl and butyl esters of p-hydroxybenzoic acid. The amount of chemical preservative that can be incorporated in the composition according to the invention will generally be from 0.05 to 5%, preferably from 0.1 to 2% by weight, the amount chosen being sufficient to arrest microbial proliferation.

(iii) Water activity depressants

The composition according to the invention can also be preserved by the inclusion of a water activity depressant such as glycerol, propylene glycol, sorbitol, sugars and salts, for examples alkali metal halides, sulphates and carboxylates. When employing a water activity depressant, sufficient should be incorporated in the composition according to the invention to reduce the water activity ($a_w$) from 1 to $<0.9$, preferably to $<0.85$ and most preferably $<0.8$, the lowest of these values being that at which yeasts, moulds and fungi will not proliferate.

The Vehicle

The composition according to the invention also comprises a solid, semi-solid or liquid cosmetically and/or physiologically acceptable vehicle, to enable the inhibitor to be conveyed to the skin at an appropriate dilution. The nature of the vehicle will depend upon the method chosen for topical administration of the composition. The vehicle can itself be inert or it can possess physiological or pharmaceutical benefits of its own.

The selection of a vehicle for this purpose presents a wide range of possibilities depending on the required product form of the composition. Suitable vehicles can be classified as described hereinafter.

It should be explained that vehicles are substances which can act as diluents, dispersants, or solvents for the inhibitor which therefore ensure that they can be applied to and distributed evenly over the hair and/or scalp at an appropriate concentration. The vehicle is preferably one which can aid penetration of the esters into the skin to reach the immediate environment of the hair follicle. Compositions according to this invention can include water as a vehicle, and/or at least one cosmetically acceptable vehicle other than water.

Vehicles other than water that can be used in compositions according to the invention can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, ispropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polythylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The amount of vehicle in the composition, including water if present, should preferably be sufficient to carry at least a portion of a selected inhibitor to the skin in an amount which is sufficient effectively to enhance hair growth. The amount of the vehicle can comprise the balance of the composition, particularly where little or no other ingredients are present in the composition. Accordingly, the vehicle or vehicles can comprise from 1 to 99.99%, preferably from 50 to 99.5% and ideally from 90 to 99% by weight of the composition.

Perfume

The composition according to the invention can also optionally comprise a perfume in an amount sufficient to make the composition acceptable to the consumer and pleasant to use. Usually, the perfume will form from 0.01 to 10% by weight of the composition.

Activity Enhancer

The composition according to the invention can also optionally comprise an activity enhancer.

The activity enhancer can be chosen from a wide variety of molecules which can function in different ways to enhance the hair growth effects of the inhibitor. Particular classes of activity enhancers include other hair growth stimulants, penetration enhancers and cationic polymers, whose presence can further improve the delivery of the inhibitor through the stratum corneum to its site of action in the immediate environment of the hair follicle.

Some activity enhancers can also function as vehicles for the inhibitor.

a) Other Hair Growth Stimulants (i). Examples of other substances which themselves possess the ability to stimulate or increase hair growth include, for example:

Benzalkonium chloride
Benzethonium chloride
Phenol
Estradiol
Diphenhydramine hydrochloride
Chlorpheniramine maleate
Chlorophyllin derivatives
Cholesterol
Salicylic acid
Cystine
Red pepper tincture
Benzyl nicotinate
dl-Menthol
Peppermint oil
Calcium pantothenate
Penthenol
Castor oil
Hinokitiol
Prednisolone
Resorcinol (ii) Further substances which themselves possess the ability to increase the rate of terminal hair growth include:

$\alpha$-1,4 esterified disaccharides described by Choay S. A. in EP-A-0 064 012, having the structure (2):

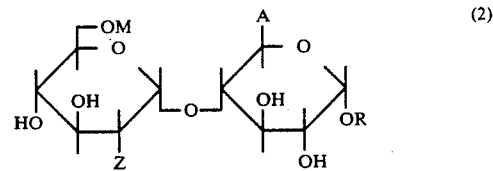

where
Z represents a functional nitrogen group, such as an azide or a group having the structure —NHB, in which B represents —H or a functional group such as acetyl or sulphate as a salt with an organic or mineral cation;
M represents —H or $SO_3M_1$, where $M_1$ is an organic or metallic cation, particularly an alkali metal; or an acetyl group;
R represents a $C_1$ to $C_4$ alkyl radical, especially methyl; or an aryl radical;
A represents a functional group such as an acid or —$COOR_1$, where $R_1$ represents —H or a $C_1$ to $C_4$ alkyl radical, especially methyl; or a metal, especially an alkali metal;
esterified oligosaccharides as described by Unilever in EP-A-0 211 610, including at least one esterified disaccharide unit consisting of a uronic acid residue having the structure (3):

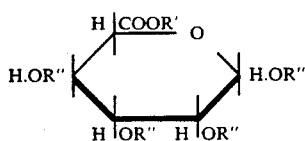
(3)

and a hexosamine residue having the structure (4):

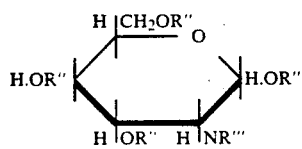
(4)

where
R' is —H, $C_3$ to $C_{10}$ alkyl or

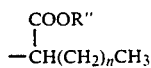

R" is —H, $C_1$ to $C_4$ alkyl, —CO(CH$_2$)$_m$CH$_3$, —SO$_3$M,
R''' is —H, —CO(CH$_2$)$_m$CH$_3$, or —SO$_3$M,
M is —H, or a metallic or organic cation
n is 0 or an integer of from 1 to 7, and
m is 0 or the integer 1 or 2;
the groups designated R" being the same or different, one R" group from each pyranose ring structure being linked by a glycosidic linkage having the configuration α-1,3, α-1,4, β-1,3 or β-1,4; and the —COOR', —CH$_2$OR"and —OR" groups being of either configuration with respect to the pyranose rings;

(iii) Minoxidil glucuronides, as described by Unilever in EP-0 242 967, (iv) Minoxidil sulphates, as described by The Upjohn Co. in WO 86/04231, and (v) Minoxidil, and other derivatives thereof as described by The Upjohn Co, in U.S. Pat. No. 4,139,619.

Particularly preferred mixtures of minoxidil and an ester according to the invention include the following:
Minoxidil and 1,1-dicyano-2-(3,4-dihydroxyphenyl-)ethylene
Minoxidil and 1,1-dicyano-2-(3-methoxy-4,5-dihydroxyphenyl) ethylene
Minoxidil and 1-amido-1-cyano-2-(3,4-dihydroxyphenyl) ethylene
Minoxidil and 1-thioamido-1-cyano-2-(3,4-dihydroxyphenyl) ethylene
Minoxidil and 1,1-dicyano-2-hydroxy-2-(3,4,5-trihydroxyphenyl)ethylene.

(vi) Direct proteoglycanase inhibitors, such as 1,10-phenanthroline.

(vii) Glycosaminoglycanase inhibitors, such as aldonolactones and esterified aldonolactones having the structure (5):

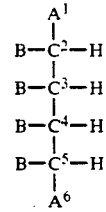
(5)

where
$A^1$ and $A^6$ are —H, —CH$_3$,

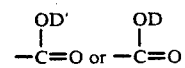

B is —OD" or a lactone linkage to position 1 or 6, or —NHCOCH$_3$
and where D is —H or $C_2$ to $C_8$ alkyl,
D' is the remainder of the molecule joined through another C atom at positions 2 to 5 to form a lactone,
D" is —H or $C_2$ (i.e. acetyl) to $C_4$ acyl of either configuration with respect to the backbone of this molecule;
preferred examples of which include:
L-Galactono-1,4-lactone
L-Arabino-1,5-lactone
D-Fucono-1,5-lactone
D-Glucaro-1,4-lactone
D-Glucurono-6,3-lactone
Galactaric acid lactone
2-Acetamido-2-deoxygluconolactone
2-Acetamido-2-deoxygalactono-lactone
D-Glucaro-1,4:6,3-dilactone
L-Idaro-1,4-lactone
2,3,5-Tri-0-acetyl-D-glucaro-1,4-lactone
2,5-Di-0-acetyl-D-glucaro-1,4:6,3-dilactone (viii) Glycosaminoglycanase inhibitors, such as monosaccharides and esterified monosaccharides having the structure (6):

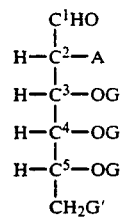
(6)

where
A is —OG or —NHCOCH$_3$
G is —H, —SO$_3$M", $C_2$ (i.e. acetyl) to $C_4$ acyl
G' is —H or —OG
M" is —H or a metal cation
wherein the functional groups can be in either configuration with respect to the backbone of the above molecule;
preferred examples of which include:
N-Acetylglucosamine
N-Acetylgalactosamine
D-Galactosamine
D-Glucosamine-3-sulphate
N-Acetylmannosamine (ix) glycosaminoglycan chain cellular uptake inhibitors such as, hexuronic acid and esters thereof which may be represented by the generic structure (7):

$$\begin{array}{c} C^1HO \\ | \\ H-C^2-OG \\ | \\ H-C^3-OG \\ | \\ H-C^4-OG \\ | \\ H-C^5-OG \\ | \\ C^6O_2D \end{array} \quad (7)$$

where
G is —H, —SO$_3$M", C$_2$ (i.e. acetyl) to C$_4$ acyl;
D is —H or C$_2$ to C$_8$ alkyl
M" is —H or a metal cation;
wherein the functional groups can be in either configuration with respect to the backbone of the above molecule;

(x) Chemical inhibitors of glycosidase activity chosen from lactams having the structure (8):

$$\begin{array}{c} A^6 \\ | \\ Q-C^5-H \\ | \\ Q-C^4-H \\ | \\ Q-C^3-H \\ | \\ Q-C^2-H \\ | \\ A^1 \end{array} \quad (8)$$

where
A$^1$ and A$^6$ are —H, —CH$_3$, $$\begin{array}{cc} OT & -NH \\ | & | \\ -C=O, -CH_2OT \text{ or} & -C=O. \end{array}$$

A$^1$ and A$^6$ being the same or different, and at least one of which being the group:

$$\begin{array}{c} -NH \\ | \\ -C=O \end{array}$$

in a lactam ring;
and where Q is —OT', —NHT' or a lactam linkage to A$^1$ or A$^6$;
the Q groups being the same or different, and at least one of which is involved in a lactam linkage;
and where T is the same or different and is chosen from
—H, —C$_p$H$_{2p+1}$ or a metal ion,
T' is —H or —COC$_p$H$_{2p+1}$, and
p is an integer of from 1 to 22;
provided that:
where any of the Q groups is
—OT' or —NHT',
then that group or groups can be of either stereochemical configuration with respect to the plane of the ring,
preferred examples of which include:
D-glucaro-1,5-lactam
L-Galactono-1,4-lactam,
L-Arabino-1,5-lactam,
D-Fucono-1,5-lactam,
D-Glucaro-1,4-lactam,
D-Glucurono-6,3-lactam,
1,2,5-tri-0-acetyl-D-glucurono-6,3-lactam
2-Acetamido-2-deoxygluconolactam.
2-Acetamido-2-deoxygalactonolactam,
D-Glucaro-1,4:6,3-dilactam,
L-Idaro-1,4-lactam,
2,3,5-Tri-0-acetyl-D-glucaro-1,4-lactam.
2,5-Di-0-acetyl-D-Glucaro-1,4:6,3-dilactam,
D-glucaro-1,5-lactam ethyl ester;

(xi) chemical activators of protein kinase C enzymes chosen from diacylglycerols having the structure (9):

$$\begin{array}{c} H_2-C-OH \\ | \\ H-C-OX \\ | \\ H_2-C-OX \end{array} \quad (9)$$

where
X is the same or different and is represented by the grouping:

$$\begin{array}{c} O \\ \| \\ -C-[(CH_2)_x. (CH=CH)_y]CH_3 \end{array} \quad (9a)$$

where x is 0 or an integer of from 1 to 28, and
y is 0 or an integer of from 1 to 5;
the R groups being of either stereochemical configuration with respect to the carbon backbone of the glycerol molecule, the double bonds being of either cis or trans configuration;
preferred examples of which include:
1,2-Dibutanoyl-rac-glycerol
1,2-Dihexanoyl-sn-glycerol
1,2-Dioctanoyl-rac-glycerol
1,2-Dioctanoyl-sn-glycerol
1,2-Didecanoyl-rac-glycerol
1-Oleoyl-2-acetyl-rac-glycerol
1-Oleoyl-2-acetyl-sn-glycerol
1-Stearoyl-2-arachidonoyl-sn-glycerol
1,2-Distearoyl-rac-glycerol
1,2-Dipentadecanoyl-sn-glycerol
1,2-dipentadecanoyl-rac-glycerol
1,2-Dipalmitoyl-rac-glycerol
1,2-Dipalmitoyl-sn-glycerol
1,2-Diseptadecanoyl-rac-glycerol
1,2-Dioleoyl-sn-glycerol
1,2-Dioleoyl-rac-glycerol
1,2-Diarachidonoyl-sn-glycerol
1,2-Dieicosanoyl-sn-glycerol
1,2-Didoeicosanoyl-rac-glycerol, and
1,2-Dioctaeicosanoyl-sn-glycerol.

(b) Penetration Enhancers

As has been stated earlier, the presence of a penetration enhancer can potentiate the benefit of the inhibitor, by improving its delivery through the stratum corneum to its site of action in the immediate environment of the hair follicle close to the dermal papilla.

The penetration enhancer can accordingly function in a variety of ways. It can for example, improve the distribution of the inhibitor on the skin surface or, it can increase its partition into the skin from the composition when applied topically, so aiding its passage to its site of action. Other mechanisms enhancing the benefit of the inhibitor may also be involved.

Examples of penetration enhancers include:
2-methyl propan-2-ol
Propan-2-ol
Ethyl-2-hydroxypropanoate
Hexan-2,5-diol
POE(2) ethyl ether
Di(2-hydroxypropyl) ether
Pentan-2,4-diol
Acetone
POE(2) methyl ether
2-hydroxypropionic acid
2-hydroxyoctanoic acid
Propan-1-ol
1,4 Dioxane
Tetrahydrofuran
Butan-1,4-diol
Propylene glycol dipelargonate
Polyoxypropylene 15 stearyl ether
Octyl alcohol
POE ester of oleyl alcohol
Oleyl alcohol
Lauryl alcohol
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibutyl suberate
Dioctyl azelate
Debenzyl sebacate
Dibutyl phthalate
Dibutyl azelate
Ethyl myristate
Dimethyl azelate
Butyl myristate
Dibutyl succinate
Didecyl phthalate
Decyl oleate
Ethyl caproate
Ethyl salicylate
Isopropyl palmitate
Ethyl laurate
2-ethyl-hexyl pelargonate
Isopropyl isostearate
Butyl laurate
Benzyl benzoate
Butyl benzoate
Hexyl laurate
Ethyl caprate
Ethyl caprylate
Butyl stearate
Benzyl salicylate
2-hydroxypropanoic acid
2-hyroxyoctanoic acid,
    Further examples of penetration enhancers include:
Dimethyl sulphoxide
N,N-Dimethyl acetamide
N,N-Dimethyl formamide
2-Pyrrolidone
1-Methyl-2-pyrrolidone
5-Methyl-2-pyrrolidone
1,5-Dimethyl-2-pyrrolidone
1-Ethyl-2-pyrrolidone
Phosphine oxides
Sugar esters
Tetrahydrofurfural alcohol
Urea
diethyl-m-toluamide, and
1-Dodecylazacyloheptan-2-one Further examples of penetration enhancers include surface active agents, preferred examples of which include:

| | |
|---|---|
| (i) | Anionic surface active agents, such as metallic or alkanolamine salts of fatty acids for example sodium laurate and triethanolamine oleate; alkyl benzene sulphonates, for example triethanolamine dodecyl benzene sulphonate; alkyl sulphates, for example sodium lauryl sulphate; alkyl ether sulphates, for example sodium lauryl ether sulphate [2 to 8 EO]; sulphosuccinates, for example sodium dioctyl sulphosuccinate; monoglyceride sulphates, for example sodium glyceryl monostearate monosulphate; isethionates, for example sodium isethionate; methyl taurides, for example Igepon T; acylsarcosinates, for example sodium myristyl sarcosinate; acyl peptides, for example Maypons and Lamepons; acyl lactylates, polyalkoxylated ether glycollates, for example trideceth-7 carboxylic acid; phosphates, for example sodium dilauryl phosphate. |
| (ii) | Cationic surface active agents, such as amine salts, for example sapamin hydrochloride; quartenary ammonium salts, for example Quaternium 5, Quaternium 31 and Quaternium 18; |
| (iii) | Amphoteric surface active agents, such as imidazol compounds, for example Miranol; N-alkyl amino acids, such as sodium cocaminopropionate and asparagine derivatives; betaines, for example cocoamidopropylbetaine |
| (iv) | Nonionic surface active agents, such as fatty acid alkanolamides, for example oleic ethanolamide; esters of polyalcohols, for example Span; polyglycerol esters, for example that esterified with $C_{12-18}$ fatty acids and one or several OH groups; polyalkoxylated derivatives, for example polyoxy:polyoxyethylene stearate, and octylphenoxy polyethoxyethanol (TRITON X-100); ethers, for example polyoxyethylene lauryl ether; ester ethers, for example Tween; amine oxides, for example coconut and dodecyl dimethyl amine oxides. |

Mixtures of two or more of the above surface active agents can be employed in the composition according to the invention.

Further examples of penetration enhancers include liposomes which can be employed to encapsulate the protein tyrosine kinase inhibitors as herein defined. Accordingly, liposomes formed from any lipid material conventionally employed in the art and of a wide variety of sizes can be incorporated in the composition according to the invention, in order to enhance the delivery of the inhibitors to the skin.

(c) Cationic polymers

Further examples of penetration enhancers include cationic polymers, preferred among which are:
Guar Hydroxypropyltrimonium chloride
Quaternium-19
Quaternium-23
Quaternium-40
Quaternium-57
Poly(dipropyldiallylammonium chloride)
Poly(methyl-$\beta$-propaniodiallylammonium chloride)
Poly(diallylpiperidinium chloride)
Poly(vinyl pyridinium chloride)

Quaternised poly (vinyl alcohol)
Quaternised poly (dimethylaminoethylmethacrylate); and
mixtures thereof The amount of activity enhancer, when employed in accordance with the invention, will normally be from 0.1 to 50%, preferably from 0.5 to 25% and most preferably from 0.5 to 10% by weight of the composition.

Other hair growth promoter adjuncts

The composition according to the invention can also contain adjuncts other than those already mentioned, depending on the form of the intended product. It is, for example, possible to include antiseptics, preservatives, antioxidants, emulsifiers and colouring agents, which can improve the stability and consumer appeal of the composition.

The composition according to the invention can also be employed as a vehicle for a wide variety of cosmetically or pharmaceutically active ingredients, particularly ingredients which have some beneficial effect other than the promotion of hair growth when applied to the skin.

Process

The invention also provides a process for the preparation of a composition suitable for topical application to mammalian skin or hair which comprises mixing a protein tyrosine kinase inhibitor, as herein defined, with a suitable vehicle to provide a composition according to the invention, in which the inhibitor forms from 0.0001 to 99% by weight of the composition.

Product Form and Container

The compositions of the invention can be formulated as liquids, for example as a lotion, shampoo, milk or cream for use in conjunction with an applicator such as a rollball applicator, or a spray device such as an aerosol can containing propellant, or a container fitted with a pump to dispense the liquid product. Alternatively, the compositions of the invention can be solid or semi-solid, for example sticks, creams or gels, for use in conjunction with a suitable applicator or simply a tube, bottle or lidded jar, or as a liquid-impregnated fabric, such as a tissue wipe.

The invention accordingly also provides a closed container containing a composition as herein defined.

Use of the protein tyrosine kinase inhibitor for Inducing, Maintaining or Increasing Hair Growth The invention also provides for the use of an inhibitor, as herein defined, for topical application to mammalian skin or hair for inducing, maintaining or increasing hair growth.

The compositions according to the invention are primarily intended for topical application to the scalp of the human subject, particularly where the head is already bald or balding, in order to promote the regrowth of terminal hair. The compositions can also be applied profilactically to the hair and hence the scalp to reduce or prevent the onset of baldness.

The amount of the composition and the frequency of application to the hair and/or scalp can vary widely, depending on personal needs, but it is suggested as an example that topical application of from 0.1 to 5g daily containing from 0.00001 to 1 g of a selected inhibitor over the period of at least six months will in most cases result in an improvement in hair growth.

EVALUATION OF EFFICACY OF PROTEIN TYROSINE KINASE INHIBITOR AS HAIR GROWTH PROMOTERS USING THE RAT MODEL

The Rat Hair Growth Test

The effect of compounds on hair growth was assessed using male albino Wistar rats as an animal model. The rats were chosen from as few litters as possible and were each approximately 42 days of age at the start of the test. Each rat was housed individually to prevent licking.

In each comparison, 10 rats were used in each group and hair growth was assessed as follows:

A small patch of normal skin (4 cm×4 cm) on the upper back of each rat was clipped at the start and 0.3 ml of a hair growth stimulant composition (or a control) applied topically twice daily and once on Saturdays and Sundays to each clipped area. The concentration of test compound in the composition was chosen from 0.01 to 20% by weight.

It is to be understood that the potency of each inhibitor in terms of its ability to induce, maintain or increase hair growth is unlikely to be uniform, some being more potent than others, and therefore the concentration of any inhibitor chosen for thorough evaluation must be carefully selected after preliminary testing to determine its potential as a hair growth promoter. In any case, this concentration will lie within the range of from 0.01 to 20% by weight as stipulated above.

Hair was clipped from the area of the patch twice weekly, collected and weighed at each time point over a standard period of 3 months, and cumulative hair weight calculated. From these data, it was possible to estimate the effect of an inhibitor as a hair growth stimulant (test compound) on the amount and duration of hair growth during the experiment. A positive response, i.e. an increase of at least 10% by weight of hair after 3 months treatment, compared with a control indicates the potential of the test compound to prevent hair loss and/or reverse baldness in human subjects.

Accordingly, when the inhibitor, as herein defined, are assessed either individually or in combination as test compound by the Rat Hair Growth Test, an increase of at least 10% by weight of hair after 3 months treatment will be obtained. Usually, the 10% by weight minimum value will be attained well before the end of this 3 months period.

EXAMPLES

The invention is illustrated by the following examples, in each of which the selected inhibitor is identified as that enumerated hereinbefore.

Example 1

This Example illustrates a lotion according to the invention which is suitable for topical application to the scalp in order to promote hair growth.

The lotion has the following formulation:

|  | % w/w |
|---|---|
| Inhibitor No. 1 | 0.1 |
| ethanol | 99.995 |
| perfume | q.s. |

Example 2

This Example illustrates a hair tonic which is suitable for application to hair or scalp.

The hair tonic has the following formulation:

|  | % w/w |
| --- | --- |
| Inhibitor No. 2 | 0.8 |
| ethanol | 50 |
| water | 49 |
| perfume | q.s. |

Example 3

This Example also illustrates a lotion which is suitable for topical application to the scalp.

The lotion has the following formulation:

|  | % w/w |
| --- | --- |
| Inhibitor No. 3 | 1.5 |
| propan-2-ol | 10 |
| ethanol | 88.5 |
| perfume | q.s. |

Example 4

This Example also illustrates a hair tonic which is suitable for application to hair or scalp.

The hair tonic has the following formulation:

|  | % w/w |
| --- | --- |
| Inhibitor No. 4 | 0.2 |
| ethanol | 40 |
| water | 59.80 |
| perfume | q.s. |

Examples 5 to 8

The following formulations represent lotions which can be used topically in the treatment of bald or balding male or female heads.

|  | % w/w | | | |
| --- | --- | --- | --- | --- |
|  | 5 | 6 | 7 | 8 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| Inhibitor No. 5 | 5 | — | — | — |
| Inhibitor No. 6 | — | 1 | — | — |
| Inhibitor No. 7 | — | — | 0.8 | — |
| Inhibitor No. 8 | — | — | — | 0.6 |
| Perfume | 1 | 1 | 1 | 1 |
| Water | to 100 | 100 | 100 | 100 |

Examples 9 to 12

The following formulations represent creams which can be used in the treatment of baldness.

|  | % w/w | | | |
| --- | --- | --- | --- | --- |
|  | 9 | 10 | 11 | 12 |
| Cetyl alcohol polyoxyethylene (10) | 4 | 4 | 4 | 4 |
| Cetyl alcohol | 4 | 4 | 4 | 4 |
| Mineral oil | 4 | 2 | — | — |
| Paraffin wax | — | 2 | 4 | — |
| Partial glyceride of palmitic and stearic acids | — | — | — | 4 |
| Inhibitor No. 9 | 2 | — | — | — |
| Inhibitor No. 10 | — | 1.5 | — | — |
| Inhibitor No. 11 | — | — | 2 | — |
| Inhibitor No. 12 | — | — | — | 1 |
| Triethanolamine | 0.75 | 0.75 | 0.75 | 0.75 |
| Butane-1,3-diol | 3 | 3 | 3 | 3 |
| Xanthan gum | 0.3 | 0.3 | 0.3 | 0.3 |
| Preservative | 0.4 | 0.4 | 0.4 | 0.4 |
| Perfume | q.s. | q.s. | q.s. | q.s. |
| Water | to 100 | 100 | 100 | 100 |

Example 13

This Example illustrates a water-in-oil high internal phase emulsion containing an ester according to the invention.

The emulsion consisted of 10% by volume oily phase and 90% by weight aqueous phase.

The oily phase and the aqueous phase had the following constitution:

|  | % w/w |
| --- | --- |
| Oily phase | |
| Sorbitan monooleate | 20 |
| Quaternium-18 hectorite | 5 |
| Liquid paraffin | 75 |
| Aqueous phase | |
| Inhibitor No. 13 | 0.5 |
| Xanthan gum | 1 |
| Preservative | 0.3 |
| Perfume | q.s. |
| Sodium chloride (1% w/w solution) | to 100 |

The emulsion was prepared by taking 10 parts by volume of the oily phase and to it adding slowly with stirring 90 parts by volume of the aqueous phase.

The high internal phase water-in-oil emulsion so formed can be applied topically to the scalp, to improve hair growth and regrowth.

The following examples 14 to 18 illustrate shampoos for use in washing the hair and scalp, and for promoting hair growth on the scalp.

EXAMPLE 14

|  | % w/w |
| --- | --- |
| Sodium lauryl ether sulphate (2 EO) [21% AD] | 41.4 |
| Lauryl dimethylamino acetic acid betaine: [30% AD] | 4 |
| Coconut fatty acid diethanolamine | 1.5 |
| Oleyl triethoxy phosphate (BRIPHOS 03D) | 1 |
| Polyglycol-polyamine condensation resin (POLYQUART H) [50% active] | 1.5 |
| Preservative, colouring matter, salt | 0.58 |
| Inhibitor No. 14 | 5 |
| Perfume | q.s. |
| Water | to 100 |

Example 15

|  | % w/w |
| --- | --- |
| Sodium lauryl ether sulphate (2 EO) | 12 |

| | % w/w |
|---|---|
| [100% AD] | |
| POLYMER JR400 | 2.5 |
| BRIPHOS O3D | 2.5 |
| Inhibitor No. 15 | 4 |
| Magnesium Sulphate | 5 |
| Perfume | q.s. |
| Water | to 100 |

Example 16

This Example also illustrates a lotion which is suitable for topical application to the scalp.
The lotion has the following formulation:

| | % w/w |
|---|---|
| Inhibitor No. 16 | 1.5 |
| propan-2-ol | 10 |
| ethanol | 88.5 |
| perfume | q.s. |

Example 17

This Example also illustrates a hair tonic which is suitable for application to hair or scalp.
The hair tonic has the following formulation:

| | % w/w |
|---|---|
| Inhibitor No. 17 | 0.2 |
| ethanol | 40 |
| water | 59.80 |
| perfume | q.s. |

Example 18

| | % w/w |
|---|---|
| Monoethanolamine lauryl sulphate: [100% AD] | 20 |
| JAGUAR C13S | 3 |
| BRIPHOS O3D | 1.7 |
| Coconut diethanolamide | 5 |
| Inhibitor No. 18 | 1 |
| Zinc gluconate | 3 |
| Perfume | q.s. |
| Water to | 100 |
| pH adjusted to 6.5 | |

Example 19

| | % w/w |
|---|---|
| Sodium lauryl ether sulphate (3 EO): [100% AD] | 12 |
| JAGUAR C13S | 0.3 |
| BRIPHOS O3D | 1 |
| Inhibitor No. 19 | 2 |
| Sodium chloride | 4 |
| Perfume | q.s. |
| Water to | 100 |
| pH adjusted to 6.5 | |

Example 20

| | % w/w |
|---|---|
| Sodium lauryl ether sulphate (2 EO) | 12 |

| | % w/w |
|---|---|
| [100% AD] | |
| POLYMER JR400 | 3 |
| BRIPHOS O3D | 1 |
| Opacifier | 9 |
| Inhibitor No. 20 | 5 |
| Perfume | q.s. |
| Water to | 100 |
| pH adjusted to 6.5 | |

Examples 21

This example illustrates a powder composition according to the invention which can be applied topically to the scalp.

| | % w/w |
|---|---|
| Chemically modified starch | 5 |
| Chemically modified cellulose | — |
| Boric acid | 10 |
| Zinc oxide | 5 |
| Inhibitor No. 21 | 3 |
| Minoxidil | 1 |
| Perfume | q.s. |
| Chalk | 10 |
| Talc to | 100 |

Example 22

The following example illustrates a lotion according to the invention which can be applied topically to the scalp to prevent hair loss and stimulate hair regrowth.

| | % w/w |
|---|---|
| Inhibitor No. 22 | 7 |
| Minoxidil | 0.2 |
| ethanol | 16 |
| citric acid | 1.05 |
| water to | 100 | pH adjusted to 4.2 with sodium hydroxide

Examples 23 & 24

These examples illustrate hair tonics which are suitable for application to the hair and scalp.
The hair tonics had the following formulation:

| | % w/w | |
|---|---|---|
| | 26 | 27 |
| Inhibitor No. 23 | 2 | — |
| Inhibitor No. 24 | — | 3 |
| ethanol | 50 | 50 |
| water | 48 | 47 |
| perfume | q.s. | q.s. |

Example 25

This example illustrates a microgel which is suitable for topical application to hair or scalp.
The gel had the following formulation:

| | % w/w |
|---|---|
| A. Polyoxyethylene (10) oleyl ether | 14.5 |
| Polyoxyethylene fatty glyceride | 14.5 |

23

-continued

|  | % w/w |
|---|---|
| Light liquid petroleum | 13.7 |
| Propylene glycol | 7.6 |
| Sorbitol | 5.9 |
| Inhibitor No. 11 | 4 |
| B. Perfume | q.s. |
| C. Water | to 100 |

This microgel was prepared by heating part A to 90° C. and part C to 95° C. and then adding part C to part A with stirring. Part B was then added at 70° C. and the final mixture cooled and poured into jars at 55° C. to 60° C. On further cooling, a gel was formed.

Example 26

This example illustrates a shampoo which is suitable for topical application to hair in order to cleanse it, at the same time delivering an inhibitor to the scalp to enhance hair growth or regrowth.

The shampoo had the following formulation:

|  | % w/w |
|---|---|
| Triethanolamine lauryl sulphate | 16.8 |
| Coconut diethanolamide | 3.0 |
| Hydroxypropylmethyl-cellulose (1) | 0.25 |
| Corn syrup (80% solids) (2) | 20.5 |
| Dimethylpolysiloxane (3) | 1.0 |
| Cationic cellulose (4) | 0.5 |
| Ethyl alcohol (SDA 40) | 9.0 |
| Vinyl carboxy polymer (5) | 0.75 |
| Inhibitor No. 12 | 1 |
| Perfume, colour, preservative | q.s. |
| Water to | 100 |
| Acid or base to pH: | 6.5 |

(1) Methocel E4M (Dow Chemical)
(2) 42 Dextrose equivalent (Staley 1300)
(3) 60,000 centistokes (Viscasil, GEC)
(4) Polymer JR 400
(5) Carbopol 941 (BF Goodrich)

Examples 27 to 28

The following formulations represent lotions which can be used topically in the treatment of bald or balding male or female heads.

|  | % w/w | |
|---|---|---|
|  | 27 | 28 |
| Hydroxyethyl cellulose | 0.4 | — |
| Absolute ethanol | 25 | 25 |
| Propane-1,2-diol | — | — |
| Butane-1,3-diol | 38.4 | 38.8 |
| Paramethyl benzoate | 0.2 | 0.2 |
| Inhibitor No. 11 | 5 | — |
| Inhibitor No. 12 | — | 1 |
| Perfume | 1 | 1 |
| Water to | 100 | 100 |

Example 29

Inhibitor 11 was used in a test of ability to block the action of epidermal growth factor (EGF) on hair follicles.

Inhibitor 11 was prepared as a 100 mM solution in dimethyl sulphoxide (DMSO). To make a test solution this was diluted to 40 μM. Consequently the resulting test solution also contained 0.04% DMSO. The same concentration of DMSO was used in control solutions.

24

Human hair follicles were isolated from female skin (removed during facelift operations) and placed in tissue culture medium. Such follicles were placed in individual wells of a culture plate and there exposed to one of four aqueous solutions. All four of these solutions were based on the same tissue culture medium augmented with 1% foetal calf serum. Some of the solutions contained 40 μM of inhibitor 11 and/or 10 ng/ml of EGF. All of them contained 0.04% DMSO. These additions to the tissue culture medium are indicated in the table below.

Follicles were cultured in the solutions for 48 hours then examined for characteristic features of entry into the catagen phase. The follicles were scored as being in anagen phase, catagen phase or intermediately between.

The experiment was carried out three times using varying numbers of follicles. The total number of follicles exposed to each solution was 42. The average of the results from all three experiments is set out in the following table, together with the compositions used.

|  | Solution no: | | | |
|---|---|---|---|---|
|  | 1 | 2 | 3 | 4 |
| Additions to culture medium: | | | | |
| DMSO | 0.04% | 0.04% | 0.04% | 0.04% |
| EGF | — | 10 ng/ml | 10 ng/ml | — |
| Inhibitor 11 | — | — | 40 μm | 40 μm |
| % in each phase: | | | | |
| Anagen | 85.7% | 0% | 19.0% | 83.3% |
| Intermediate | 11.9% | 54.8% | 73.9% | 16.7% |
| Catagen | 2.4% | 45.2% | 7.1% | 0% |

Comparison of the results with solutions 1 and 2 illustrates the known ability of EGF to induce catagen. Comparison of the results with solutions 2 and 3 shows the effect of inhibitor 11 which is to delay the induction of catagen.

I claim:

1. A method of inhibiting phase transition from anagen to catagen in mammalian hair growth, comprising applying to hair or skin in a region of the scalp a composition which comprises:

(i) as a protein tyrosine kinase inhibitor from 0.0001 to 99% by weight of an aryl-substituted ethylene having the structure (1)

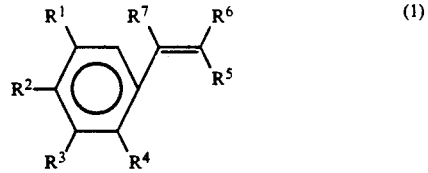

(1)

where $R^1$, $R^2$, $R^3$ and $R^4$ are the same or different, and are selected from a group consisting of $$-H, -OH, -OC_nH_{2n+1}, -NO_2, -Cl, -Br, -F \text{ and } -\overset{O}{\underset{\|}{C}}H;$$

where $R^5$ and $R^6$ are the same or different, and are selected from a group consisting of

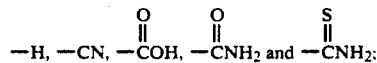

where $R^7$ is chosen from —H and —OH; and
where n is an integer of from 1 to 8; and
(ii) from 1 to 99.999% by weight of a cosmetically acceptable vehicle for the inhibitor.

2. A method according to claim 1, in which the inhibitor is chosen from those in structure (1) where R is a $C_1$ to $C_{20}$ alkyl group.

3. A method according to claim 1 in which the inhibitor is chosen from:
1-carboxy-2-(4-hydroxyphenyl)ethylene
1,1-dicarboxy-2-(4-hydroxyphenyl)ethylene
1,1-dicyano-2-(4-hydroxyphenyl)ethylene
1-carboxy-2-(3,4-dihydroxyphenyl)ethylene
1,1-dicyano-2-(3-hydroxyphenyl)ethylene
1-cyano-1-carboxy-2-(2,5-dihydroxyphenyl)ethylene
1-carboxy-1-cyano-2-(3,4-dihydroxphenyl)ethylene
1,1-dicyano-2-(3,4-dihydroxyphenyl)ethylene
1,1-dicyano-2-(3-methoxy-4,5-dihydroxyphenyl)ethylene
1,1-dicyano-2-(3,4,5-trihydroxyphenyl)ethylene
1-amido-1-cyano-2-(3,4-dihydroxyphenyl)ethylene
1-thioamido-1-cyano-2-(3,4-dihydroxyphenyl)ethylene
1-cyano-2-(4-hydroxyphenyl)ethylene
1,1-dicyano-2-(3-hydroxy-4-nitrophenyl)ethylene
1,1-dicyano-2-hydroxy-2-(4-hydroxyphenyl)ethyl<ne
1,1-dicyano-2-(3-methoxy-4-hydroxyphenyl)ethylene
1,1-dicyano-2-(3,5-dihydroxyphenyl)ethylene
1,1-dicyano-2-hydroxy-2-(3,4,5-trihydroxyphenyl)ethylene
1-carboxy-1-cyano-2-(4-methoxyphenyl)ethylene
1-carboxy-1-cyano-2-(4-fluorophenyl)ethylene
1-carboxy-1-cyano-2-(3-methoxy-4-hydroxyphenyl)ethylene
1-carboxy-1-cyano-2-(3,5-dimethoxy-4-hydroxyphenylethylene
1-carboxy-1-cyano-2-(4-hydroxyphenyl)ethylene
1-carboxy-1-cyano-2-(4-phenylcarboxyaldehyde)ethylene, and
1-cyano-1-carboxy-2-(2,5-dihydroxyphenyl)ethylene 4. A method according to claim 1 in which the inhibitor forms from 0.01 to 20% by weight of the composition.

5. A method according to claim 1, further comprising minoxidil present in an effective amount to function as a hair growth stimulant.

6. A method according to claim 1, further comprising a surface active agent present in an effective amount to function as a surfactant.

7. A method according to claim 1, further comprising a cationic polymer present in an effective amount to enhance activity of the inhibitor.

8. A method according to claim 1, wherein the composition has a pH value of from 2 to <7.

9. A method according to claim 1 which is a shampoo or hair conditioner.

10. A method of prolonging anagen phase in growth of mammalian hair, comprising applying to hair or skin in a region of the scalp a composition which comprises:

(i) as a protein tyrosine kinase inhibitor from 0.0001 to 99% by weight of an aryl-substituted ethylene having the structure (1)

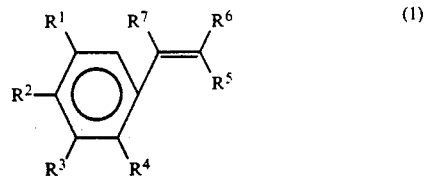

where $R^1$, $R^2$, $R^3$ and $R^4$ are the same or different, and are selected from a group consisting of

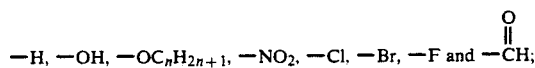

where $R^5$ and $R^6$ are the same or different, and are selected from a group consisting of

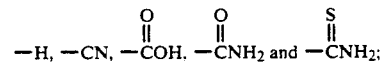

where $R^7$ is chosen from —H and —OH; and
where n is an integer of from 1 to 8; and
(ii) from 1 to 99.999% by weight of a cosmetically acceptable vehicle for the inhibitor.

11. A method of inhibiting a transition in mammalian hair growth from terminal to vellus hair, comprising applying to hair or skin in a region of the scalp a composition which comprises:

(i) as a protein tyrosine kinase inhibitor from 0.0001 to 99% by weight of an aryl-substituted ethylene having the structure (1)

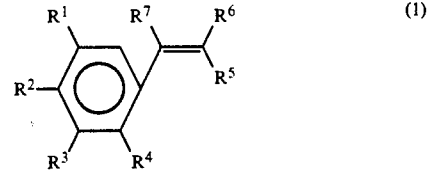

where $R^1$, $R^2$, $R^3$ and $R^4$ are the same or different, and are selected from a group consisting of

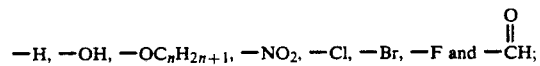

where $R^5$ and $R^6$ are the same or different, and are selected from a group consisting of

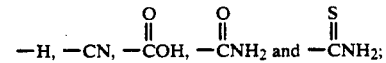

where $R^7$ is chosen from —H and —OH; and
where n is an integer of from 1 to 8; and
(ii) from 1 to 99.999% by weight of a cosmetically acceptable vehicle for the inhibitor.

* * * * *